United States Patent
Pan et al.

(10) Patent No.: US 6,628,742 B2
(45) Date of Patent: Sep. 30, 2003

(54) CARDIAC HELICAL HALF SCAN RECONSTRUCTIONS FOR MULTIPLE DETECTOR ROW CT

(75) Inventors: Tin-Su Pan, Brookfield, WI (US); Danielle Drummond, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/965,780

(22) Filed: Sep. 28, 2001

(65) Prior Publication Data

US 2002/0118790 A1 Aug. 29, 2002

Related U.S. Application Data

(60) Provisional application No. 60/237,762, filed on Sep. 29, 2000.

(51) Int. Cl.$^7$ ................................................ A61B 6/00
(52) U.S. Cl. ................................................ 378/8; 378/4
(58) Field of Search ................ 378/4, 15, 210, 378/19, 64, 165, 8

(56) References Cited

U.S. PATENT DOCUMENTS

| | | |
|---|---|---|
| 4,182,311 A | 1/1980 | Seppi et al. |
| 4,547,892 A | 10/1985 | Richey et al. |
| 4,868,747 A | 9/1989 | Mori et al. |
| 5,262,946 A | 11/1993 | Heuscher |
| 5,383,231 A | 1/1995 | Yamagishi |
| 5,694,446 A * | 12/1997 | Shinohara ........................ 378/4 |
| 5,751,782 A | 5/1998 | Yoshitome |
| 5,960,056 A | 9/1999 | Lai |
| 5,974,108 A | 10/1999 | Taguchi et al. |
| 6,072,851 A * | 6/2000 | Sivers ........................ 378/15 |
| 6,256,366 B1 * | 7/2001 | Lai ........................ 378/4 |
| 6,266,553 B1 | 7/2001 | Fluhrer et al. |
| 6,298,111 B1 | 10/2001 | Ozaki |
| 6,301,325 B1 * | 10/2001 | Besson et al. ........................ 378/15 |

FOREIGN PATENT DOCUMENTS

| | | |
|---|---|---|
| EP | 0 983 747 A1 | 3/2000 |
| WO | WO 00/30539 | 6/2000 |

OTHER PUBLICATIONS

"Multislice Helical CT: Image Temporal Resolution," Hui Hu, et al., IEEE Transactions On Medical Imaging, vol. 19, No. 5, May 2000, pp. 384–390.

(List continued on next page.)

Primary Examiner—Drew A. Dunn
Assistant Examiner—Irakli Kiknadze
(74) Attorney, Agent, or Firm—Carl B. Morton, Esq.; Armstrong Teasdale LLP

(57) ABSTRACT

One embodiment of the present invention is a method for reconstructing cardiac images using a computed tomographic (CT) imaging system. The method includes steps of: selecting a helical scanning pitch for scanning a patient; scanning the patient, including the patient's heart, with a computed tomographic imaging system having a plurality of detector rows and a rotating gantry to acquire projection data from the plurality of detector rows; selecting a phase of the cardiac cycle for imaging; combining portions of the acquired projection data from a plurality of detector rows, the combined portions corresponding to the selected cardiac phase; and reconstructing images, including images of the patient's heart, from the combined, interpolated projection data.

20 Claims, 7 Drawing Sheets

OTHER PUBLICATIONS

"Multi–Slice Helical CT: Scan and Image Temporal Resolution," Hui Hu, et al., Imaging Tech, Inc., 20720 W. Watertown Rd., Suite 201, Waukesha, WI 53186; General Electric Company, P.O. Box 414, NB–922, Milwaukee, WI 53201.

Technical Notes, Dennis L. Parker, "Optimal Short Scan Convolution Reconstruction for Fanbeam CT," pp. 254–257.

Dennis L. Parker, "Optimization of Short Scan Convolution Reconstruction in Fan Beam CT," IEEE Proceedings, International Workshop on Physics and Engineering in Medical Imaging, Mar. 15–18, 1982, Pacific Grove, CA., pp. 199–202.

U.S. Patent Application of Pan, et al., for "Hybrid Reconstruction for High Pitch Multi–Slice Helical Cardiac Imaging," Serial No. 09/429,867, filed Oct. 29, 1999.

International Search Report, dated May 3, 2002, Application No. PCT/US 01/30595, 3 pages.

* cited by examiner

CARDIAC HELICAL HALF SCAN RECONSTRUCTIONS FOR MULTIPLE DETECTOR ROW CT

CROSS REFERENCE TO RELATED APPLICATIONS

This application claims the benefit of U.S. Provisional Application No. 60/237,762 filed Sep. 29, 2000.

BACKGROUND OF THE INVENTION

This invention relates generally to methods and apparatus for reconstruction of computed tomography (CT) images, and more particularly to methods and apparatus for rapid acquisition of projection data for high resolution reconstruction of CT images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the object being scanned is not moved, and the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Helical scanning is used in some CT imaging systems, as are multislice detectors. During helical scans, a patient is placed on a moving table, which transports the patient through an opening in the rotating gantry. The direction of movement is referred to as the z-axis of the imaging system, and a multislice detector of such a system has multiple parallel rows of detector elements. The rows themselves are stacked in the z-direction, so that projection data acquired by each row corresponds to a "slice" of a patient. For axial scans, the plane of each slice is perpendicular to the z-axis if an axial scan is performed. The detector elements of adjacent rows of known multislice detector arrays abut one another, and are characterized by a spacing distance between their centers. When a helical scan is performed, the table moves a selectable distance during one gantry rotation. The ratio of the z-axis movement during one gantry rotation to the z-axis spacing between centers of the detector elements in each row is defined as the "helical pitch" that characterizes a given scan. (For a single row detector array, the z-axis spacing is replaced by the thickness of the single row in the z-axis direction.)

During a helical scan, projection data is collected during transport of the patient through the rotating gantry. With appropriate image reconstruction techniques, helical scans provide a relatively efficient way of imaging a volume of a patient that is thicker along the z-axis than the combined thickness of the rows of a multislice detector.

In some CT imaging applications such as cardiac imaging, a body part being imaged is not stationary. In the cardiac imaging case, it is necessary to use EKG gating to reconstruct images with data from a particular phase of a cardiac cycle. However, imaging an entire heart typically requires scanning a patient volume having a thickness of 12 cm, which is quite large in relation to the total thickness that can be imaged by known multislice CT detector arrays. In addition, projection data from a sufficient span of view angles is required for CT image reconstruction of any selected cardiac cycle phase. These requirements work to reduce the maximum helical pitch that can be used for cardiac scanning. However, with a low pitch helical scan, it may be difficult for a patient to hold his or her breath long enough during the scan to avoid additional body movement that would reduce the resolution of reconstructed images. Also, because low pitches translate directly into longer scanning times, patient dose is increased.

One known method for efficiently reconstructing image data from helical scans is known as a "half scan" reconstruction method. This method takes advantage of redundancy inherent in scanned data by using only projection data acquired during one-half rotation (180 degrees) of the CT gantry plus one fan angle. (A fan angle is defined as the maximum angular extent of the acquired projection data, which depends on the angular width of the CT radiation beam and/or the angular extend of the detector array.) However, known reconstruction methods utilizing helical scan half scan reconstruction use the data from all the rows of detector elements to produce a single image per cardiac cycle rather than multiple images per cardiac cycle.

For example, and referring to the representation of FIG. 3, at least one known CT imaging system with a four row detector produces only one image (i.e., one slice) per cardiac cycle. In FIG. 3, the vertical axis units are gantry rotations, while the horizontal axis unit is the distance between centers of detector elements in adjacent rows (in this case, 2.5 mm). Thus, time is represented on the vertical axis and z-axis distance is represented on the horizontal axis. Solid diagonal lines 102, 104, 106, and 108 represent z-axis positions of a patient scanned by each row of detector elements as a function of time, for a 3:1 pitch. In FIG. 3, the gantry speed is 0.8 seconds per rotation for a heart rate of 75 bpm, or 1.0 seconds per rotation for heart rate of 60 bpm. Projection data acquired during the time indicated by vertical bars 110, 112, 114, and 116 is used to reconstruct an image corresponding to a selected phase of the cardiac cycle of the patient being scanned. Projection data acquired four detector rows is interpolated to points on vertical bars 110, 112, 114, and 116, the centers of which lie on a midpoint of the multislice detector, which is represented by diagonal dashed line 118.

When a complete 12 cm of coverage is desired in a single breathhold of 30 seconds, reconstruction of a diastole phase or any other phase results in gaps 120 between two adjacent images of the same phase. At the 3:1 pitch represented in FIG. 3, a space of 7.5 mm is created between images. Alternatively, the pitch can be reduced, but then more than one patient breathhold will be necessary to obtain 12 cm of coverage, and patient dose is significantly increased.

It would therefore be desirable to provide methods and apparatus for reducing patient dose and for reducing gap distances between images in cardiac CT imaging scans.

BRIEF SUMMARY OF THE INVENTION

There is therefore provided, in one embodiment of the present invention, a method for reconstructing cardiac images using a computed tomographic (CT) imaging system. The method includes steps of: selecting a helical scanning pitch for scanning a patient; scanning the patient, including the patient's heart, with a computed tomographic imaging system having a plurality of detector rows and a rotating gantry to acquire projection data from the plurality of detector rows; selecting a phase of the cardiac cycle for imaging; combining portions of the acquired projection data from a plurality of detector rows, the combined portions corresponding to the selected cardiac phase; and reconstructing images, including images of the patient's heart, from the combined, interpolated projection data.

This and other embodiments of the present invention are effective in reducing patient dose by allowing helical scans at higher pitches, and for reducing gap distances between images in cardiac CT imaging scans.

DETAILED DESCRIPTION OF THE INVENTION

Figure 1:
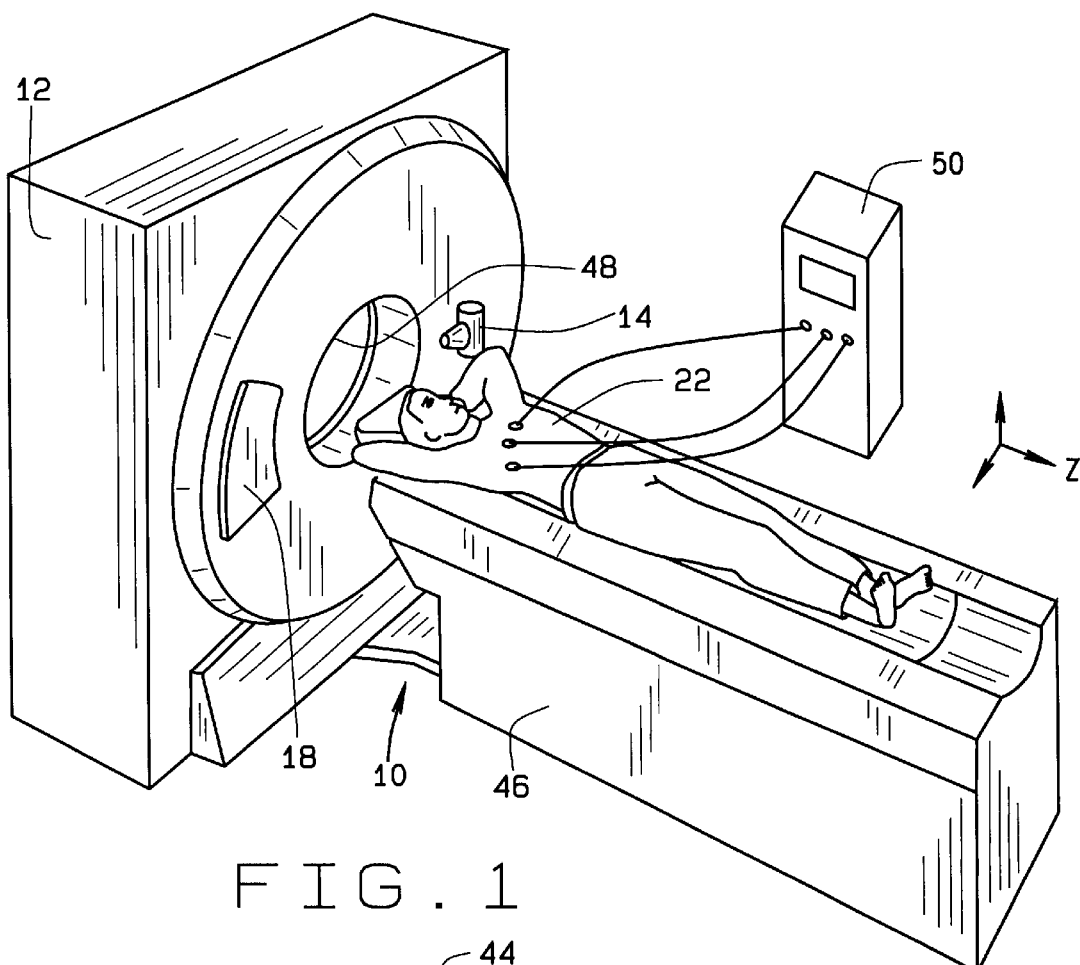
FIG. 1 is a pictorial view of a CT imaging system.
Figure 2:
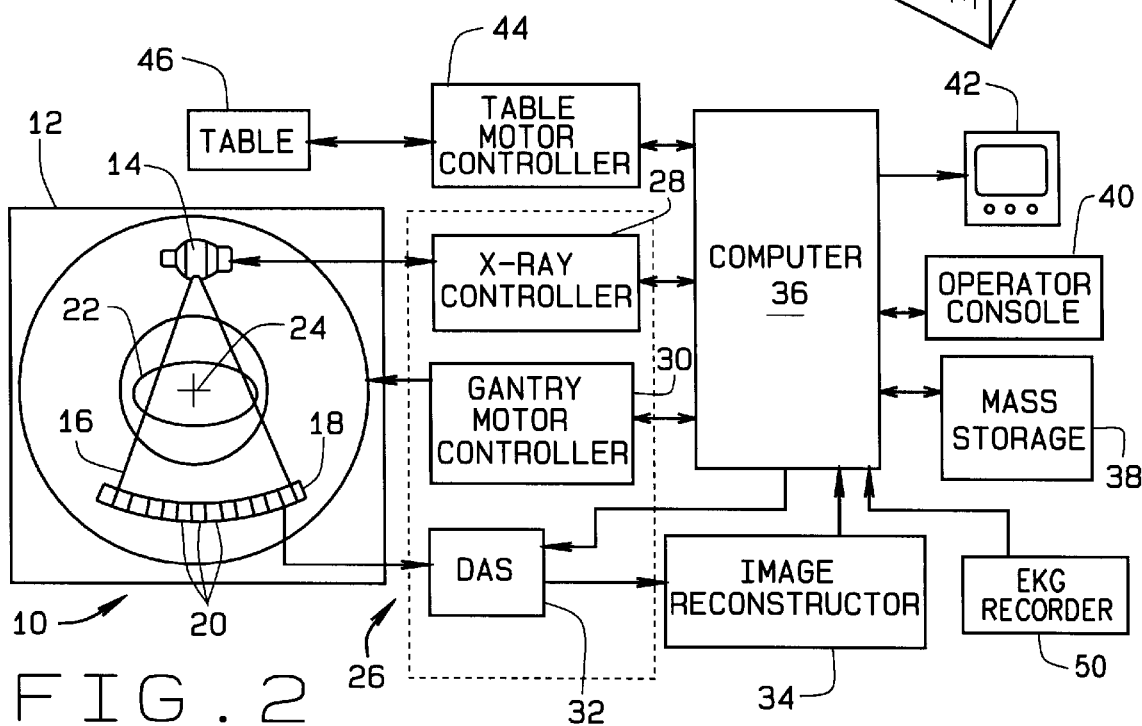
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. The direction of motion of the table defines the z-axis of imaging system 10. The multiple rows of detector array 18 are stacked in the z-axis direction so that, during an axial scan, projection data is acquired from a number of parallel slices of a volume of patient 22. The parallel slices define planes that are perpendicular in the z-direction, when an axial scan is performed.

In one embodiment of image reconstruction of the present invention, EKG data from EKG machine 50 is taken synchronously with the scan data and interpreted to determine cardiac cycle rate and phase. A set of reconstruction parameters are calculated based on a user selected cardiac phase for reconstruction and percentage overlap. Default values are provided to simplify operation, e.g., a cardiac phase 0.47 of a cycle from a leading R-peak for a 0.8 sec gantry speed (i.e., 0.8 seconds per gantry rotation) and 50% overlap. A helical pitch is determined that is a function of the selected (or default) values. The reconstruction then obtains a set of images from the beginning of the scan with the specified (or default) phase and overlap. The set of images thus reconstructed covers an entire heart without any gap. The images are reconstructed with half scan reconstructions, and are thus referred to as cardiac helical (CH) half scan reconstructions.

To ensure a complete coverage with no gap between cardiac cycles, the reconstruction pitch pitch satisfies a relationship written as:

$$\text{pitch} \leq \frac{(nss-1)}{\left(\frac{60}{bpm*gsp} + \frac{2}{3}\right)}, \tag{1}$$

where nss is the total number of detector rows, bpm is the cardiac rate in beats per minute, and gsp is the gantry speed in seconds per rotation. Eq. 1 corresponds to a criterion written as:

$$2(D-d) > S \qquad (2)$$

where $$D = \frac{nss - 1}{2}, \; d = \frac{pitch}{3}, \; \text{and} \; S = \frac{60 * pitch}{bpm * gsp}.$$

Eq. 1 sets a maximum pitch. A minimum pitch is determined as the pitch required to scan the entire cardiac region (about 12 cm along the z-axis) in one breathhold, or about 30 to 40 seconds.

Figure 3:
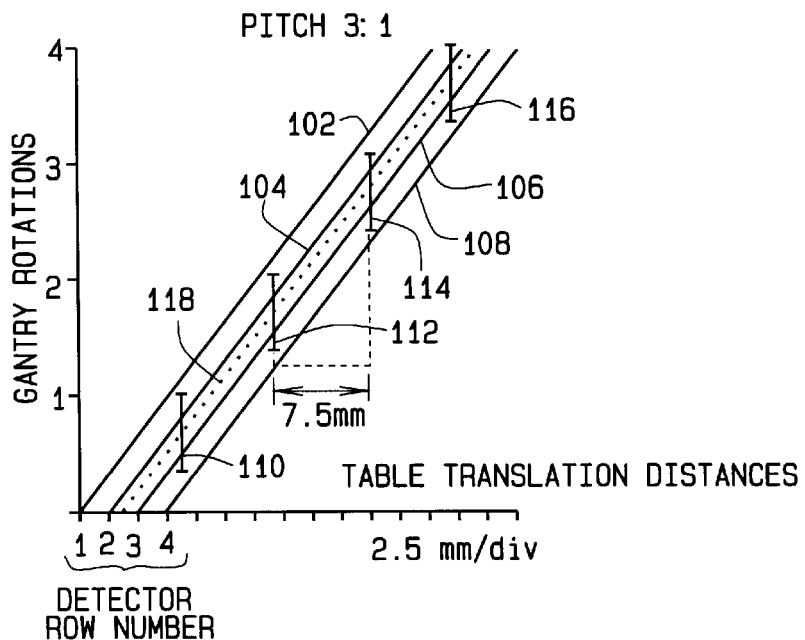
FIG. 3 is a representation of a prior art cardiac imaging scan at 3:1 helical pitch, showing loci of points used to reconstruct images of a selected cardiac cycle phase.
Figure 4:
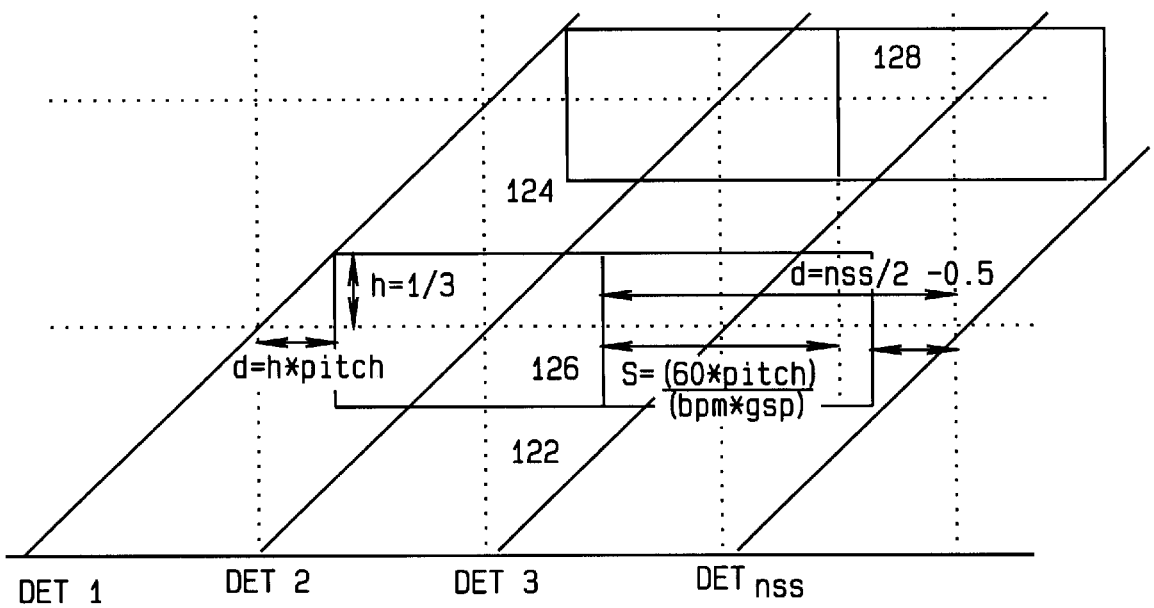
FIG. 4 is a representation of one image reconstruction method embodiment of the present invention, showing reconstruction boxes within which only interpolation of projection data is required for reconstructing an image.

FIG. 4 illustrates the criterion of eq. 2 on a chart similar to that of FIG. 3. In FIG. 4, the horizontal axis unit is the detector row spacing, and the vertical axis is the number of gantry rotations. For the four detector row imaging system 10 represented by FIG. 4, a "half scan" reconstruction requires projection data from ⅔ of a gantry rotation, so that h=⅓. Each box 122 and 124 thus represents a region within which data for reconstruction of an image of heart at a selected phase of the cardiac cycle can be performed without data extrapolation. (In FIG. 4, the cardiac rate is determined using EKG machine 50 of FIG. 2 and gantry 12 rotation speed is synchronized to the cardiac rate.) Each vertical line segment 126 and 128 that bisects boxes 122 and 124, respectively, represents a locus of interpolated projection data that can be, and in one embodiment is used to reconstruct an image. The criterion of eq. 2 ensures that there is no z-axis gap between boxes of reconstruction regions of two adjacent cardiac cycles. More particularly, the variable S in eq. 2 represents a distance between the centers 126 and 128 of two adjacent reconstruction boxes 122 and 124 and is heart rate dependent (a higher heart rate corresponds to a shorter S). The variable D is one half of the span of a detector row along the z-axis, and is dependent on the number of slices acquired (more slices corresponds to a larger D). The variable d corresponds to an area that would have to be sacrificed to potential image quality degradation were linear extrapolation used to provide data necessary for reconstruction. The value of d is pitch dependent (i.e., higher values of pitch correspond to larger areas sacrificed).

In one embodiment of the present invention, to further reduce spatial imaging gaps, more than one image is reconstructed for each reconstruction box 122, 124. For example, two or three images are reconstructed at different z-axis positions along spaced-apart vertical loci inside each reconstruction box. Even when only a single slice is reconstructed per box 122, 124, the locus of interpolated points used for reconstruction need only be a vertical line segment within the box and need not necessarily bisect the box.

It will be understood that the descriptions given here refer to only a small amount of the plurality of reconstruction boxes needed for a full cardiac scan because it is impractical to illustrate all the gantry revolutions of a full cardiac scan in the figures. However, the concepts described herein need only be repeated for each reconstruction box of a full scan.

The criterion of eq. 2 can be applied to any number of slices and is modified in various embodiments for different field of view sizes, and is useful for obtaining maximum pitch for gantry speeds of 1.0, 0.8, and 0.5 sec per rotation. Tables I, II and III list pitch selection and scan times for this embodiment for 120 mm coverage with 4 detector rows and 2.5 mm collimation for 1.0, 0.8, and 0.5 sec gantry speeds, respectively. In general, for equal heart rates, the faster the gantry speed, the smaller the pitch, and the shorter the scan time due to a lower area d. Also, for the same gantry speed, the higher the heart rate, the higher the pitch.

TABLE I

Cardiac Helical (CH) Reconstruction, 2.50 mm collimation, 1.0 sec gantry speed

| bpm | pitch | time |
|-----|-------|------|
| 40  | 1.4   | 35   |
| 50  | 1.6   | 30   |
| 60  | 1.8   | 27   |
| 70  | 2.0   | 24   |
| 80  | 2.1   | 23   |
| 90  | 2.3   | 21   |
| 100 | 2.4   | 20   |
| 110 | 2.5   | 19   |
| 120 | 2.6   | 19   |

TABLE II

Cardiac Helical (CH) Reconstruction, 2.50 mm collimation, 0.8 sec gantry speed

| bpm | pitch | time |
|-----|-------|------|
| 40  | 1.2   | 33   |
| 50  | 1.4   | 28   |
| 60  | 1.6   | 25   |
| 70  | 1.7   | 22   |
| 80  | 1.9   | 21   |
| 90  | 2.0   | 19   |
| 100 | 2.1   | 18   |
| 110 | 2.2   | 17   |
| 120 | 2.3   | 17   |

TABLE III

Cardiac Helical (CH) Reconstruction, 2.50 mm collimation, 0.5 sec gantry speed

| bpm | pitch | time |
|-----|-------|------|
| 40  | 0.8   | 29   |
| 50  | 1.0   | 25   |
| 60  | 1.1   | 21   |
| 70  | 1.3   | 19   |
| 80  | 1.4   | 17   |
| 90  | 1.5   | 16   |
| 100 | 1.6   | 15   |
| 110 | 1.7   | 14   |
| 120 | 1.8   | 13   |

In eq. 2, $$d = \frac{pitch}{3}$$

was selected to ensure that no z-extrapolation occurred in the helical weighting. In one embodiment, pitch is increased, and a small portion of data for image reconstruction is obtained by extrapolation without any significant degradation of the image quality. The degradation that does occur is not likely to be observed in cardiac imaging due to the effects of cardiac motion and continuous translation of the imaging table. However, a slight degradation of image quality can be observed when a stationary phantom is scanned. By the addition of one quarter of detector width, $$d = \frac{\text{pitch}}{3} - \frac{1}{4},$$

and the new pitch criteria pitch$_{1/4}$ in this embodiment is written:

$$\text{pitch}_{\frac{1}{4}} \leq \frac{\left(nss - \frac{1}{2}\right)}{\left(\frac{60}{bpm * gsp} + \frac{2}{3}\right)} \quad (3)$$

Tables IV, V, and VI list pitch selection and scan times for this embodiment for 120 mm coverage with 4 detector rows and 2.5 mm collimation for 1.0, 0.8, and 0.5 sec gantry speeds, respectively.

TABLE IV

Cardiac Helical (CH) Reconstruction + 1/4, 2.50 mm collimation, 1.0 sec gantry speed

| bpm | pitch | time |
|---|---|---|
| 40 | 1.6 | 30 |
| 50 | 1.9 | 26 |
| 60 | 2.1 | 23 |
| 70 | 2.3 | 21 |
| 80 | 2.5 | 19 |
| 90 | 2.6 | 18 |
| 100 | 2.8 | 17 |
| 110 | 2.9 | 17 |
| 120 | 3.0 | 16 |

TABLE V

Cardiac Helical (CH) Reconstruction + 1/4, 2.50 mm collimation, 0.8 sec gantry speed

| bpm | pitch | time |
|---|---|---|
| 40 | 1.4 | 28 |
| 50 | 1.6 | 24 |
| 60 | 1.8 | 21 |
| 70 | 2.0 | 19 |
| 80 | 2.2 | 18 |
| 90 | 2.3 | 16 |
| 100 | 2.5 | 16 |
| 110 | 2.6 | 15 |
| 120 | 2.7 | 14 |

TABLE VI

Cardiac Helical (CH) Reconstruction + 1/4, 2.50 mm collimation, 0.5 sec gantry speed

| bpm | pitch | time |
|---|---|---|
| 40 | 1.0 | 25 |
| 50 | 1.1 | 21 |
| 60 | 1.3 | 18 |
| 70 | 1.5 | 16 |
| 80 | 1.6 | 15 |
| 90 | 1.8 | 14 |
| 100 | 1.9 | 13 |
| 110 | 2.0 | 12 |
| 120 | 2.1 | 11 |

In another embodiment of the present invention, an additional percentage separation $$s\left(\text{say } 50\% = \frac{1}{2}\right)$$

with respect to one detector row width of the two boxes shown in FIG. 4. This is to simulate an overlap (say 50%) that is likely to occur in most of the image reconstructions, but is not identical to the overlap in a helical reconstruction. There is no guarantee in this embodiment that image selection will not fall into this separation. However, for comparison purpose, a criterion for this for this embodiment is written as $$2(D-d)+s>S \quad (4)$$

where $$d = \frac{\text{pitch}}{3} - \frac{1}{4}.$$

From this, a higher pitch limitation for pitch¼ is obtained, which is now a function of s. This limitation is written as:

$$\text{pitch}_{\frac{1}{4}}(s) \leq \frac{\left(nss - s + \frac{1}{2}\right)}{\left(\frac{60}{bpm * gsp} + \frac{2}{3}\right)} \quad (5)$$

Images scanned with this pitch should be examined to verify that no significant image degradation has occurred.

Tables VII, VIII, and IX list pitch selection and scan times for this embodiment for 120 mm coverage with 4 detector rows and 2.5 mm collimation for 1.0, 0.8, and 0.5 sec gantry speeds, respectively.

TABLE VII

Cardiac Helical (CH) Reconstruction + 1/4 (s = 0.5), 2.50 mm collimation, 1.0 sec gantry speed

| bpm | pitch | time |
|---|---|---|
| 40 | 1.8 | 26 |
| 50 | 2.1 | 22 |
| 60 | 2.4 | 20 |
| 70 | 2.6 | 18 |
| 80 | 2.8 | 17 |
| 90 | 3.0 | 16 |
| 100 | 3.2 | 15 |
| 110 | 3.3 | 15 |
| 120 | 3.4 | 14 |

TABLE VIII

Cardiac Helical (CH) Reconstruction + 1/4 (s = 0.5), 2.50 mm collimation, 0.8 sec gantry speed

| bpm | pitch | time |
|---|---|---|
| 40 | 1.6 | 24 |
| 50 | 1.8 | 21 |
| 60 | 2.1 | 18 |
| 70 | 2.3 | 17 |
| 80 | 2.5 | 15 |
| 90 | 2.7 | 14 |
| 100 | 2.8 | 14 |

TABLE VIII-continued

Cardiac Helical (CH) Reconstruction + 1/4 (s = 0.5), 2.50 mm collimation, 0.8 sec gantry speed

| bpm | pitch | time |
|---|---|---|
| 110 | 3.0 | 13 |
| 120 | 3.1 | 12 |

TABLE IX

Cardiac Helical (CH) Reconstruction + 1/4 (s = 0.5), 2.50 mm collimation, 0.5 sec gantry speed

| bpm | pitch | time |
|---|---|---|
| 40 | 1.1 | 22 |
| 50 | 1.3 | 18 |
| 60 | 1.5 | 16 |
| 70 | 1.7 | 14 |
| 80 | 1.8 | 13 |
| 90 | 2.0 | 12 |
| 100 | 2.1 | 11 |
| 110 | 2.3 | 11 |
| 120 | 2.4 | 10 |

It will be observed that, in different embodiments of the present invention, different pitch selections are employed. In one embodiment, there is always overlap between the two adjacent cardiac cycles to ensure complete coverage. In another embodiment, an extrapolation of ¼ of a detector row width provided for trading off image quality for scan speed. In a third embodiment, over ¼ of the detector width in z is used for extrapolation, allowing some images to (at least potentially) fall in a separation. Because of the degradation in image quality that may occur using the third embodiment, the first two of the three embodiments would usually be preferred.

In one embodiment, a CH reconstruction method is used to reconstruct images without any helical pitch limitation. In this embodiment, image reconstruction uses two input parameters, one being a view offset and the other being a position in a cardiac phase that starts the first view of a view offset and continues for a number of views covering ⅔ of a gantry rotation for half scan reconstruction. In one embodiment corresponding to a special case in which view offset is the only parameter, a z-position is automatically chosen as the center of the z-coverage for a selected cardiac phase. Therefore, for this special case, the CH reconstruction reduces to a known implementation of helical half scan reconstruction.

Image quality in CH reconstruction depends on the helical pitch selected. In another embodiment of the present invention, a hybrid reconstruction is used to provide increased image quality at the highest pitches.

Cardiac motion is relatively periodic between any two consecutive cardiac cycles when no significant arrhythmia is present. Therefore, in one embodiment of present invention, a hybrid helical half scan reconstruction (HCH) reconstructs one image in part from a first cardiac cycle and in part from a second cardiac cycle, i.e., corresponding phases of two consecutive cardiac cycles. Each cardiac cycle is capable of producing an equal number of images spaced at a detector row spacing, i.e., coverage per cardiac cycle is (nss–1) detector rows. Thus, helical half scan reconstruction provides the same scan efficiency as helical full scan reconstruction. HCH reconstruction is particularly desirable for cardiac helical half scan reconstruction when $$2D > S \qquad (6)$$

and $$\text{pitch} \leq \frac{(nss-1)}{\left(\frac{60}{bpm*gsp}\right)} = \frac{(nss-1)*bpm*gsp}{60}. \qquad (7)$$

Tables X, XI, and XII list pitch selection and scan times for this HCH embodiment for 120 mm coverage with 4 detector rows and 2.5 mm collimation for 1.0, 0.8, and 0.5 sec gantry speeds, respectively.

TABLE X

Hybrid Cardiac Helical (HCH) Reconstruction, 2.50 mm collimation, 1.0 sec gantry speed

| bpm | pitch | time |
|---|---|---|
| 40 | 2.0 | 24 |
| 50 | 2.5 | 19 |
| 60 | 3.0 | 16 |
| 70 | 3.5 | 14 |
| 80 | 4.0 | 12 |
| 90 | 4.5 | 11 |
| 100 | 5.0 | 10 |
| 110 | 5.5 | 9 |
| 120 | 6.0 | 8 |

TABLE XI

Hybrid Cardiac Helical (HCH) Reconstruction, 2.50 mm collimation, 0.8 sec gantry speed

| bpm | pitch | time |
|---|---|---|
| 40 | 1.6 | 24 |
| 50 | 2.0 | 19 |
| 60 | 2.4 | 16 |
| 70 | 2.8 | 14 |
| 80 | 3.2 | 12 |
| 90 | 3.6 | 11 |
| 100 | 4.0 | 10 |
| 110 | 4.4 | 9 |
| 120 | 4.8 | 8 |

TABLE XII

Hybrid Cardiac Helical (HCH) Reconstruction, 2.50 mm collimation, 0.5 sec gantry speed

| bpm | pitch | time |
|---|---|---|
| 40 | 1.0 | 24 |
| 50 | 1.3 | 19 |
| 60 | 1.5 | 16 |
| 70 | 1.8 | 14 |
| 80 | 2.0 | 12 |
| 90 | 2.3 | 11 |
| 100 | 2.5 | 10 |
| 110 | 2.8 | 9 |
| 120 | 3.0 | 8 |

Tables XIII, XIV, and XV list pitch selection and scan times for this HCH embodiment for 120 mm coverage with 4 detector rows and 1.25 mm collimation for 1.0, 0.8, and 0.5 sec gantry speeds, respectively.

TABLE XIII

Hybrid Cardiac Helical (HCH) Reconstruction,
1.25 mm collimation, 1.0 sec gantry speed

| bpm | pitch | time |
|---|---|---|
| 40 | 2.0 | 48 |
| 50 | 2.5 | 38 |
| 60 | 3.0 | 32 |
| 70 | 3.5 | 27 |
| 80 | 4.0 | 24 |
| 90 | 4.5 | 21 |
| 100 | 5.0 | 19 |
| 110 | 5.5 | 17 |
| 120 | 6.0 | 16 |

TABLE XIV

Hybrid Cardiac Helical (HCH) Reconstruction,
1.25 mm collimation, 0.8 sec gantry speed

| bpm | pitch | time |
|---|---|---|
| 40 | 1.6 | 48 |
| 50 | 2.0 | 38 |
| 60 | 2.4 | 32 |
| 70 | 2.8 | 27 |
| 80 | 3.2 | 24 |
| 90 | 3.6 | 21 |
| 100 | 4.0 | 19 |
| 110 | 4.4 | 17 |
| 120 | 4.8 | 16 |

TABLE XV

Hybrid Cardiac Helical (HCH) Reconstruction,
1.25 mm collimation, 0.5 sec gantry speed

| bpm | pitch | time |
|---|---|---|
| 40 | 1.0 | 48 |
| 50 | 1.3 | 38 |
| 60 | 1.5 | 32 |
| 70 | 1.8 | 27 |
| 80 | 2.0 | 24 |
| 90 | 2.3 | 21 |
| 100 | 2.5 | 19 |
| 110 | 2.8 | 17 |
| 120 | 3.0 | 16 |

In this embodiment, pitch is dependent only on heart rate and gantry speed, so that the total scan time is the same for any given heart rate.

Figure 5:
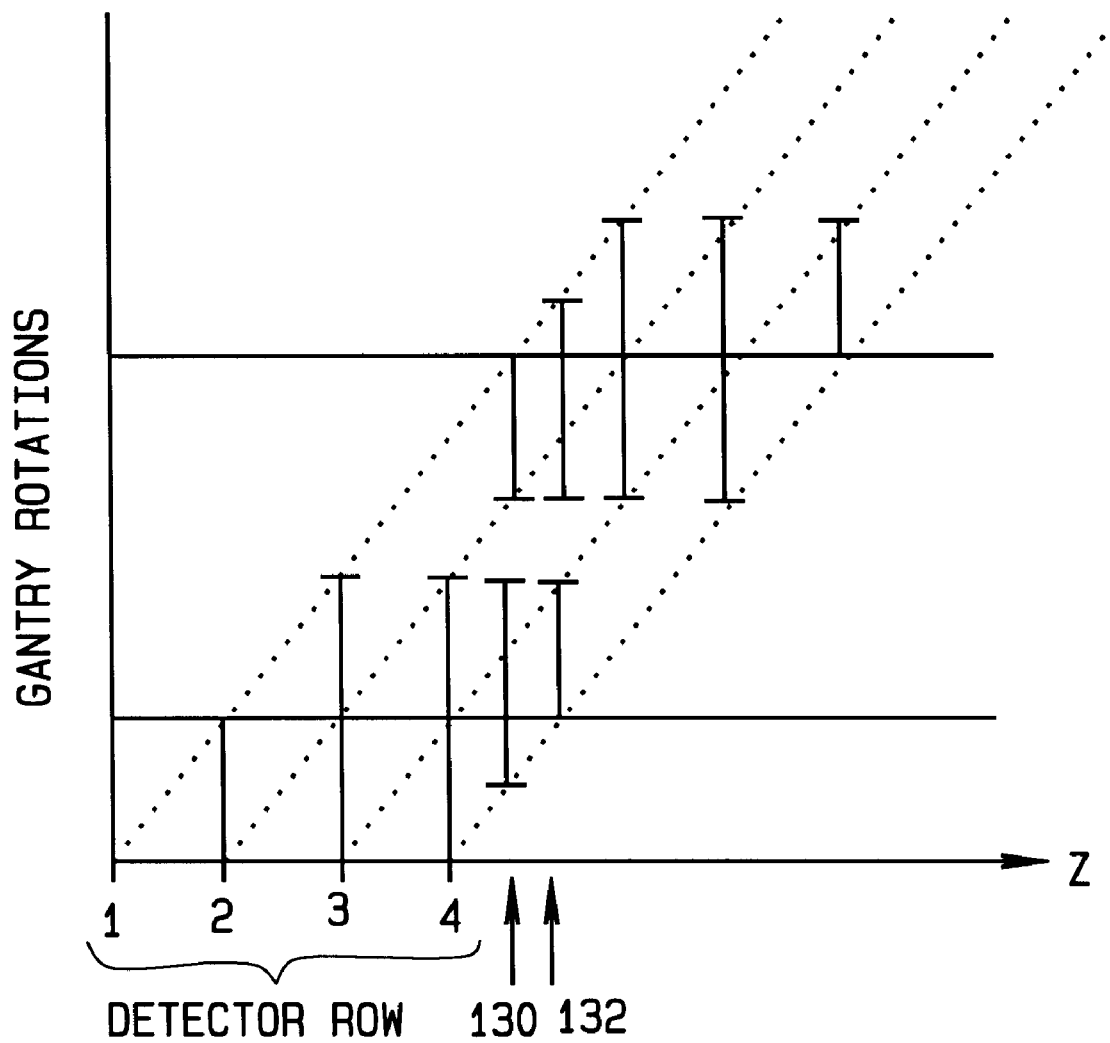
FIG. 5 is a representation of a scan showing data utilization from two cardiac cycles in hybrid helical half scan (HCH) reconstruction.

It is possible to have more than a 100% contribution from each of the two cardiac cycles in this embodiment. FIG. 5 shows a representation of this possible configuration. When data are sufficient for reconstruction at z-axis locations of detector rows 3 and 4 of a four-row detector, HCH reconstruction simplifies to the CH reconstruction. When data are not sufficient for reconstruction of an image, extrapolation is required to make up data from the same z-location, such as at z-locations indicated by arrows 130, 132. An HCH reconstruction of any image at a z-location between arrows 130, 132 uses a portion of the data acquired during a first cardiac cycle and a portion of data acquired during a second cardiac cycle. For an image at arrow 130, the first cardiac cycle contributes about ¾ of the data, while the second cardiac cycle contributes as much as ½ of the data. For an image at arrow 132, contributions are ½ and ¾ from the first and the second cardiac cycles, respectively. In known CT imaging system reconstruction, only data from the cardiac cycle having the largest contribution would be used fully. Data from the other cardiac cycle would be used only when there is not enough data for reconstruction in the cycle having the larger contribution.

In one embodiment, the whole contribution of the cycle contributing the most is used, and the remainder is supplemented by the other cardiac cycle. Therefore, if ¾ and ½ are the contributions from two cycles, the reconstruction will use ¾ and ¼ from the two cycles. There is a smoothing of 31 views applied between the data from the two cardiac cycles.

The HCH reconstruction reduces to the CH reconstruction in cases in which the helical scanning pitch is so small that, at all locations for reconstruction, 100% of the data is obtainable from any one cardiac cycle.

Figure 6:
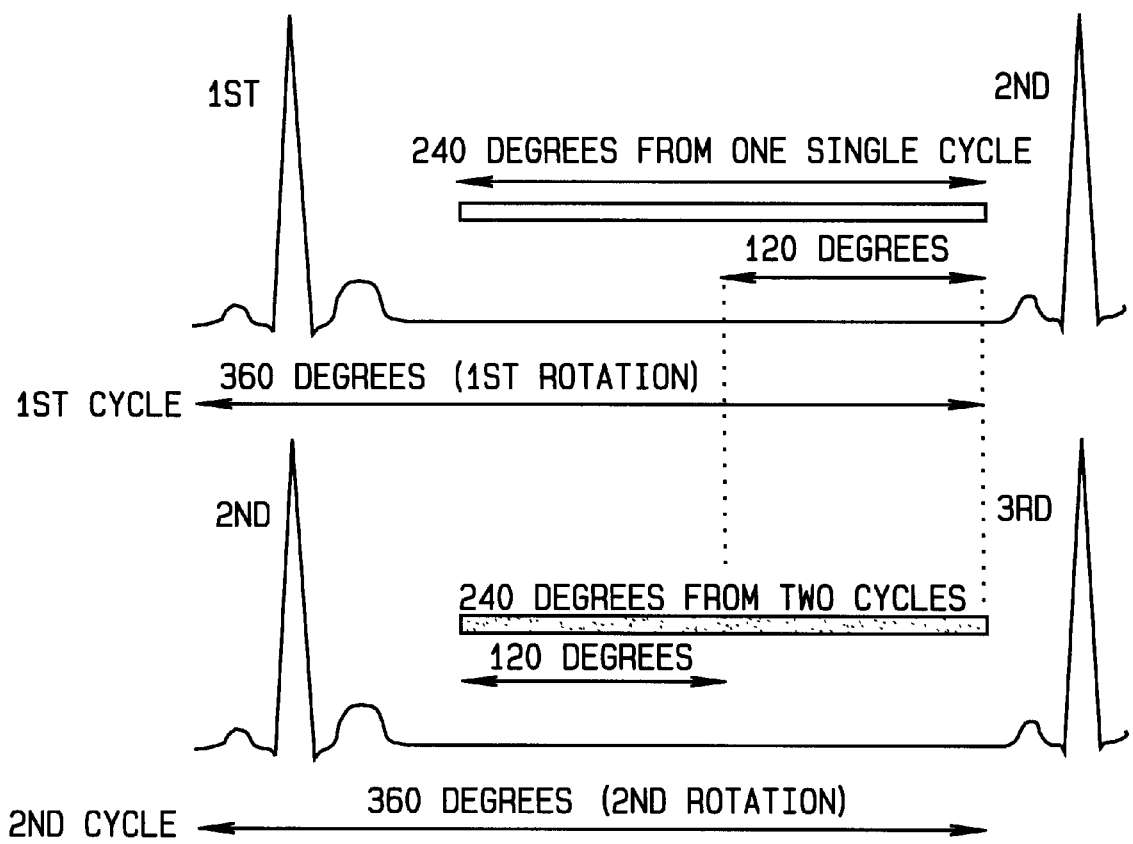
FIG. 6 is a representation of successive cardiac cycles when the cardiac cycle is the same as the gantry rotation rate.
Figure 7:
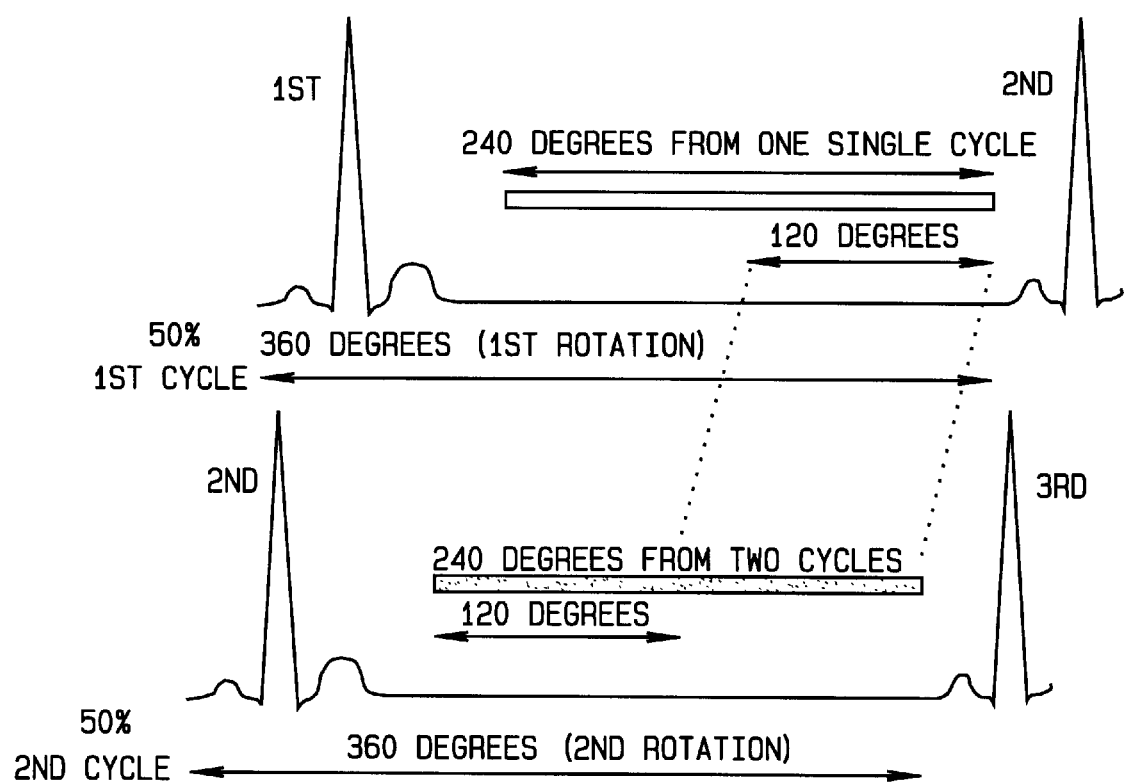
FIG. 7 is a representation of successive cardiac cycles when the cardiac cycle is less than the gantry rotation rate.
Figure 8:
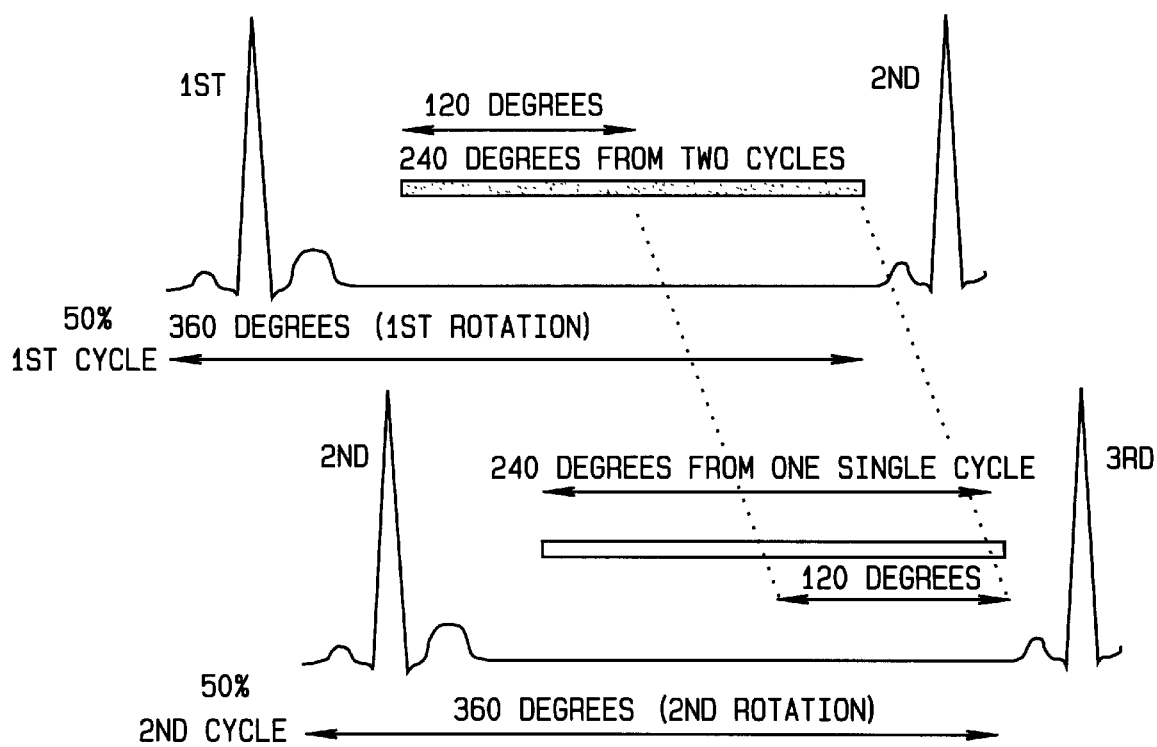
FIG. 8 is a representation of successive cardiac cycles when the cardiac cycle is greater than the gantry rotation rate.

Using HCH reconstruction for cardiac imaging allows higher helical pitches to be used in a scan. Thus, scan times are shortened and patient dosage is reduced. In addition, 3-D rendering is improved with a smooth transition of images from one cardiac cycle to the next. Also, temporal resolution is improved when the gantry rotation cycle is not synchronous to the cardiac cycle, as illustrated in FIGS. 6, 7, and 8. Because of averaging between two cardiac cycles, contrast enhancement will have an averaging effect. An image that uses data from the current and previous cardiac cycle will have contrast enhancement. An image that uses data from the current and the next cardiac cycle will have contrast reduction.

Figure 9:
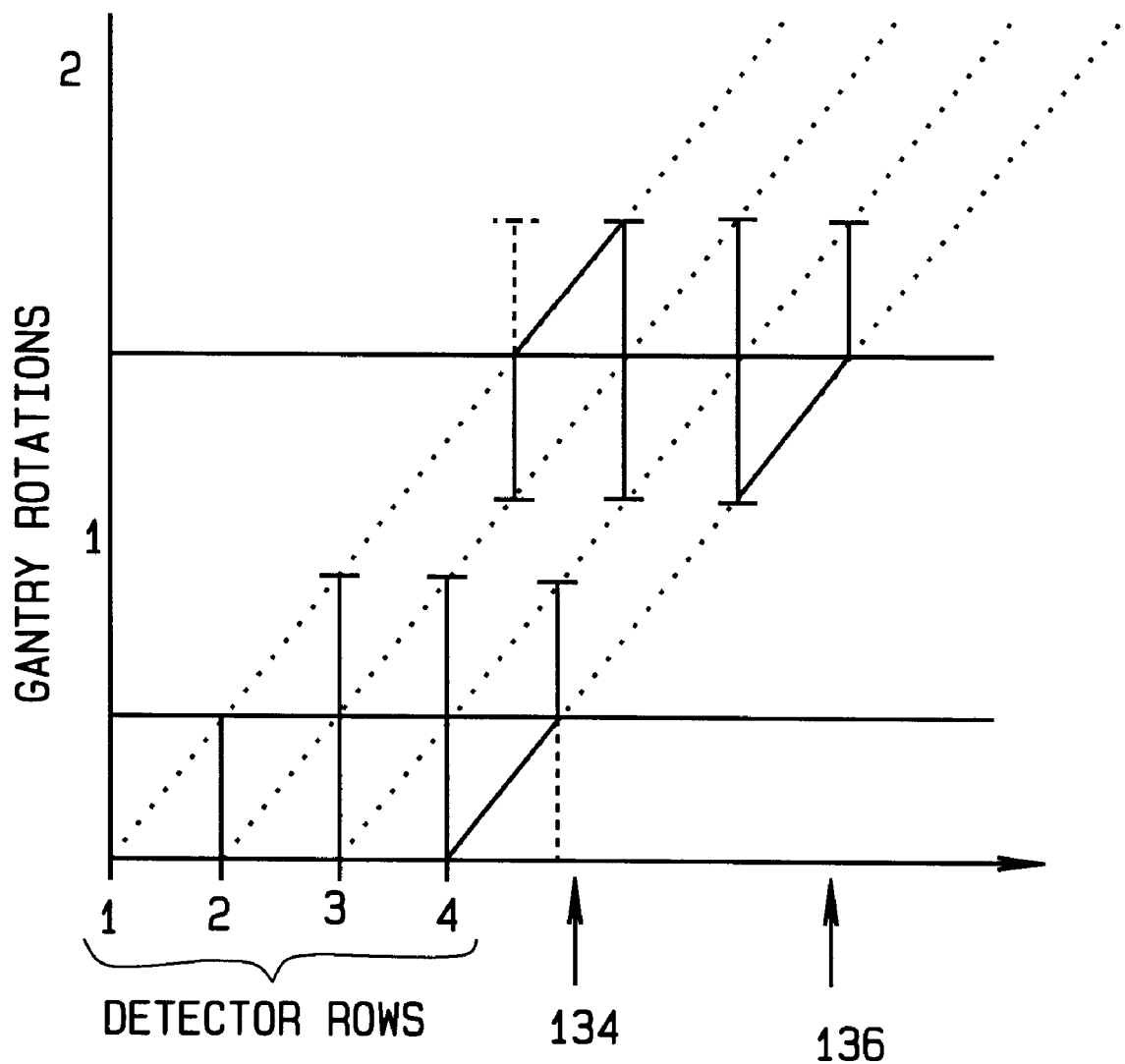
FIG. 9 is a representation of a scan in which images can be reconstructed completely from one cardiac cycle at some z-locations and at other locations using significant extrapolation.

In yet another embodiment of the present invention, images are reconstructed complete from one cardiac cycle. FIG. 9 represents a scan of a four detector row imaging system 10. Images from such a scan are reconstructed complete from one cardiac cycle at z-locations of detector rows 3 and 4. At z-locations identified by arrows 134 and 136, images are reconstructed by data from either two cycles as in HCH or CH reconstruction, with significant extrapolation.

It will thus be recognized that embodiments of the present invention described herein provide methods and apparatus for reducing patient dose and for reducing gap distances between images in cardiac CT imaging scans.

While the invention has been described in terms of various specific embodiments, those skilled in the art will recognize that the invention can be practiced with modification within the spirit and scope of the claims.

What is claimed is:

1. A method for reconstructing cardiac images using a computed tomographic (CT) imaging system, said method comprising the steps of:

selecting a helical scanning pitch for scanning a patient;

scanning the patient, including the patient's heart, with a computed tomographic imaging system having a plurality of detector rows and a rotating gantry to acquire projection data from the plurality of detector rows;

selecting a phase of the cardiac cycle for imaging;

combining portions of the acquired projection data from a plurality of detector rows, the combined portions corresponding to the selected cardiac phase; and reconstructing images, including images of the patient's heart, from the combined, interpolated projection data, wherein said step of reconstructing images comprises performing cardiac helical half scan reconstructions (CH), and wherein selecting a helical scanning pitch comprises selecting a helical scanning pitch pitch having a maximum value not greater than:

$$\text{pitch} \leq \frac{(nss-1)}{\left(\frac{60}{bpm*gsp}+\frac{2}{3}\right)},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold.

2. A method in accordance with claim 1 wherein said combining is performed exclusively by interpolation.

3. A method in accordance with claim 1 wherein the CT imaging system has a z-axis, said pitch and cardiac phase selection defines a series of reconstruction boxes for interpolation, and said reconstruction step comprises the step of reconstructing a plurality of images at spaced-apart z-axis locations for each reconstruction box, and said combining is performed exclusively by interpolation.

4. A method for reconstructing cardiac images using a computed tomographic (CT) imaging system, said method comprising the steps of:

selecting a helical scanning pitch for scanning a patient;

scanning the patient, including the patient's heart, with a computed tomographic imaging system having a plurality of detector rows and a rotating gantry to acquire projection data from the plurality of detector rows;

selecting a phase of the cardiac cycle for imaging;

combining portions of the acquired projection data from a plurality of detector rows, the combined portions corresponding to the selected cardiac phase; and reconstructing images, including images of the patient's heart, from the combined, interpolated projection data, wherein said step of reconstructing images comprises performing cardiac helical half scan reconstructions (CH), and wherein selecting a helical scanning pitch comprises selecting a helical scanning pitch pitch having a maximum value not greater than:

$$pitch_{1/4} \leq \frac{\left(nss-\frac{1}{2}\right)}{\left(\frac{60}{bpm*gsp}+\frac{2}{3}\right)},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold.

5. A method in accordance with claim 4 wherein said combining is performed using both interpolation and extrapolation.

6. A method in accordance with claim 4 wherein the CT imaging system has a z-axis, said pitch and cardiac phase selection defines a series of reconstruction boxes for interpolation, and said reconstruction step comprises the step of reconstructing a plurality of images at spaced-apart z-axis locations for each reconstruction box, and said combining step includes both interpolation and extrapolation.

7. A method for reconstructing cardiac images using a computed tomographic (CT) imaging system, said method comprising the steps of:

selecting a helical scanning pitch for scanning a patient;

scanning the patient, including the patient's heart, with a computed tomographic imaging system having a plurality of detector rows and a rotating gantry to acquire projection data from the plurality of detector rows;

selecting a phase of the cardiac cycle for imaging;

combining portions of the acquired projection data from a plurality of detector rows, the combined portions corresponding to the selected cardiac phase;

reconstructing images, including images of the patient's heart, from the combined, interpolated projection data, wherein said step of reconstructing images comprises performing cardiac helical half scan reconstructions (CH); and selecting an image separation parameter s, wherein said selecting a helical scanning pitch comprises selecting a helical scanning pitch pitch having a maximum value not greater than:

$$pitch_{1/4}(s) \leq \frac{\left(nss-s+\frac{1}{2}\right)}{\left(\frac{60}{bpm*gsp}+\frac{2}{3}\right)},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold.

8. A method in accordance with claim 7 wherein said combining is performed using both interpolation and extrapolation.

9. A method in accordance with claim 7 wherein the CT imaging system has a z-axis, said pitch and cardiac phase selection defines a series of reconstruction boxes for interpolation, and said reconstruction step comprises reconstructing a plurality of images at spaced-apart z-axis locations for each reconstruction box, and said combining step includes both interpolation and extrapolation.

10. A method for reconstructing cardiac images using a computed tomographic (CT) imaging system, said method comprising the steps of:

selecting a helical scanning pitch for scanning a patient;

scanning the patient, including the patient's heart, with a computed tomographic imaging system having a plurality of detector rows and a rotating gantry to acquire projection data from the plurality of detector rows;

selecting a phase of the cardiac cycle for imaging;

combining portions of the acquired projection data from a plurality of detector rows, the combined portions corresponding to the selected cardiac phase; and reconstructing images, including images of the patient's heart, from the combined, interpolated projection data, wherein said step of reconstructing images comprises performing cardiac helical half scan reconstructions (CH), and wherein selecting a helical scanning pitch comprises selecting a helical scanning pitch pitch having a maximum value not greater than:

$$pitch \leq \frac{(nss-1)}{\left(\frac{60}{bpm*gsp}\right)} = \frac{(nss-1)*bpm*gsp}{60},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold, and said step of combining comprises combining projection data acquired during corresponding phases of two consecutive cardiac cycles.

11. A computed tomographic imaging system for reconstructing cardiac images, said imaging system comprising a plurality of detector rows and a rotating gantry, and said imaging system being configured to:

scan at a selected helical scanning pitch pitch having a maximum value not greater than:

$$pitch \le \frac{(nss-1)}{\left(\frac{60}{bpm*gsp}+\frac{2}{3}\right)},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold;

acquire projection data of the patient, including the patient's heart, from the plurality of detector rows;

correlate the acquired projection data with cardiac cycles of the patient's heart;

combine portions of the acquired projection data from the plurality of detector rows, the combined portions corresponding to a selected cardiac phase; and reconstruct images, including images of the patient's heart, from the combined, interpolated projection data, wherein to reconstruct said images, said imaging system is configured to perform cardiac helical half scan reconstructions (CH).

12. An imaging system in accordance with claim 11 configured to perform said combining exclusively by interpolation.

13. An imaging system in accordance with claim 11 having a z-axis, wherein the selected pitch and cardiac phase define a series of reconstruction boxes for interpolation, and said imaging system is configured to reconstruct a plurality of images at spaced-apart z-axis locations for each reconstruction box, and to perform said combining exclusively by interpolation.

14. A computed tomographic imaging system for reconstructing cardiac images, said imaging system comprising a plurality of detector rows and a rotating gantry, and said imaging system being configured to:

scan at a selected a helical scanning pitch pitch having a maximum value not greater than:

$$pitch_{1/4} \le \frac{\left(nss-\frac{1}{2}\right)}{\left(\frac{60}{bpm*gsp}+\frac{2}{3}\right)},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold;

acquire projection data of the patient, including the patient's heart, from the plurality of detector rows;

correlate the acquired projection data with cardiac cycles of the patient's heart;

combine portions of the acquired projection data from the plurality of detector rows, the combined portions corresponding to a selected cardiac phase; and reconstruct images, including images of the patient's heart, from the combined, interpolated projection data, wherein to reconstruct said images, said imaging system is configured to perform cardiac helical half scan reconstructions (CH).

15. An imaging system in accordance with claim 14 configured to perform said combining using a combination of interpolation and extrapolation.

16. An imaging system in accordance with claim 14 wherein said CT imaging system has a z-axis, said pitch and cardiac phase selection defines a series of reconstruction boxes for interpolation, and imaging system is configured to reconstruct a plurality of images at spaced-apart z-axis locations for each reconstruction box, and to perform said combining using a combination of both interpolation and extrapolation.

17. A computed tomographic imaging system for reconstructing cardiac images, said imaging system comprising a plurality of detector rows and a rotating gantry, and said imaging system being configured to:

scan at a helical scanning pitch selected in accordance with an image separation parameter s wherein the helical scanning pitch pitch has a maximum value not greater than:

$$pitch_{1/4}(s) \le \frac{\left(nss-s+\frac{1}{2}\right)}{\left(\frac{60}{bpm*gsp}+\frac{2}{3}\right)},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold;

acquire projection data of the patient, including the patient's heart, from the plurality of detector rows;

correlate the acquired projection data with cardiac cycles of the patient's heart;

combine portions of the acquired projection data from the plurality of detector rows, the combined portions corresponding to a selected cardiac phase; and reconstruct images, including images of the patient's heart, from the combined, interpolated projection data, wherein to reconstruct said images, said imaging system is configured to perform cardiac helical half scan reconstructions (CH).

18. An imaging system in accordance with claim 17 configured to perform said combining using both interpolation and extrapolation.

19. An imaging system in accordance with claim 17 wherein said imaging system has a z-axis, said pitch and cardiac phase selection defines a series of reconstruction boxes for interpolation, and said imaging system is configured to combine and reconstruct a plurality of images at spaced-apart z-axis locations for each reconstruction box, and is configured to perform said combining using both interpolation and extrapolation.

20. A computed tomographic imaging system for reconstructing cardiac images, said imaging system comprising a plurality of detector rows and a rotating gantry, and said imaging system being configured to:

scan at a helical scanning pitch pitch having a maximum value not greater than:

$$pitch \leq \frac{(nss-1)}{\left(\frac{60}{bpm*gsp}\right)} = \frac{(nss-1)*bpm*gsp}{60},$$

where nss is a total number of detector rows, bpm is the patient's cardiac rate in beats per minute, and gsp is the gantry speed in seconds per rotation, and a minimum value not less than a pitch required to scan an entire cardiac region of the patient in one breathhold;

acquire projection data of the patient, including the patient's heart, from the plurality of detector rows;

correlate the acquired projection data with cardiac cycles of the patient's heart;

combine portions of the acquired projection data from the plurality of detector rows, the combined portions corresponding to a selected cardiac phase; and reconstruct images, including images of the patient's heart, from the combined, interpolated projection data, wherein said imaging system being configured to combine projection data comprises said imaging system being configured to combine projection data acquired during corresponding phases of two consecutive cardiac cycles, wherein to reconstruct said images, said imaging system is configured to perform cardiac helical half scan reconstructions (CH).

* * * * *

UNITED STATES PATENT AND TRADEMARK OFFICE
CERTIFICATE OF CORRECTION

PATENT NO.    : 6,628,742 B2                                            Page 1 of 1
DATED         : September 30, 2003
INVENTOR(S)   : Tin-Su Pan et al.

It is certified that error appears in the above-identified patent and that said Letters Patent is hereby corrected as shown below:

Column 15,
Line 47, delete "selected a helical" and insert therefor -- selected helical --.

Signed and Sealed this

Third Day of February, 2004

JON W. DUDAS
*Acting Director of the United States Patent and Trademark Office*